(12) United States Patent
Wiechmann

(10) Patent No.: US 8,257,080 B2
(45) Date of Patent: Sep. 4, 2012

(54) LOW PROFILE ORTHODONTIC BITE CORRECTOR

(75) Inventor: Dirk Wiechmann, Bad Essen (DE)

(73) Assignee: 3M Innovative Properties Company, St. Paul, MN (US)

( * ) Notice: Subject to any disclaimer, the term of this patent is extended or adjusted under 35 U.S.C. 154(b) by 164 days.

(21) Appl. No.: 12/435,747

(22) Filed: May 5, 2009

(65) Prior Publication Data
US 2010/0285422 A1 Nov. 11, 2010

(51) Int. Cl.
*A61C 7/00* (2006.01)
(52) U.S. Cl. .......................................... 433/19
(58) Field of Classification Search ............ 433/18, 433/19, 21, 22
See application file for complete search history.

(56) References Cited

U.S. PATENT DOCUMENTS

| | | |
|---|---|---|
| 934,956 A | 9/1909 | Case |
| 3,618,214 A | 11/1971 | Armstrong |
| 3,690,003 A * | 9/1972 | Gerber ............................ 433/18 |
| 3,798,773 A | 3/1974 | Northcutt |
| 4,382,783 A * | 5/1983 | Rosenberg ...................... 433/19 |
| 4,386,908 A * | 6/1983 | Kurz ................................ 433/9 |
| 4,462,800 A | 7/1984 | Jones |
| 4,551,095 A | 11/1985 | Mason |
| 4,708,646 A | 11/1987 | Jasper |
| 4,795,342 A | 1/1989 | Jones |
| 4,815,972 A | 3/1989 | Howe |
| 5,183,388 A | 2/1993 | Kumar |
| 5,352,116 A | 10/1994 | West |
| 5,435,721 A | 7/1995 | Vogt |
| 5,562,445 A | 10/1996 | DeVincenzo et al. |
| 5,632,618 A | 5/1997 | Jensen |
| 5,645,423 A | 7/1997 | Collins, Jr. |
| 5,645,424 A | 7/1997 | Collins, Jr. |
| 5,651,672 A | 7/1997 | Cleary et al. |
| 5,678,990 A | 10/1997 | Rosenberg |
| 5,711,667 A | 1/1998 | Vogt |
| 5,718,576 A | 2/1998 | Schnaitter et al. |
| 5,738,514 A | 4/1998 | DeVincenzo et al. |
| 5,897,313 A | 4/1999 | Cleary et al. |
| 5,964,588 A | 10/1999 | Cleary |
| 6,053,730 A | 4/2000 | Cleary |
| 6,322,357 B1 | 11/2001 | Vogt |
| 6,558,160 B2 | 5/2003 | Schnaitter et al. |
| 6,776,614 B2 | 8/2004 | Wiechmann et al. |
| 6,913,460 B2 | 7/2005 | Cleary et al. |
| 6,928,733 B2 | 8/2005 | Rubbert et al. |
| 6,988,888 B2 | 1/2006 | Cleary |
| 7,240,528 B2 | 7/2007 | Weise et al. |
| 2001/0036615 A1 | 11/2001 | Binder |
| 2007/0178423 A1 | 8/2007 | Rubbert et al. |
| 2007/0190477 A1 | 8/2007 | Sheikh et al. |
| 2009/0035715 A1 | 2/2009 | Cleary |

OTHER PUBLICATIONS

PCT International Search Report for PCT/US2010/032919 mailed May 23, 2011.

* cited by examiner

*Primary Examiner* — Ralph Lewis
(74) *Attorney, Agent, or Firm* — James Christoff; Kevin Weber

(57) ABSTRACT

A bite corrector for moving the relative positions of the jaws includes a telescoping assembly with an outer member and an inner member received in the outer member. The outer and inner members have matching, curved configurations. Both of the members remain in close proximity to the patient's dentition during opening and closing movement of the jaws and the likelihood of contact of the bite corrector with adjacent tissue in the patient's oral cavity is reduced.

16 Claims, 2 Drawing Sheets

LOW PROFILE ORTHODONTIC BITE CORRECTOR

BACKGROUND OF THE INVENTION

1. Field of the Invention

The present invention relates to a device that is useful during the course of orthodontic treatment for correcting the position of one dental arch relative to the other. More specifically, the present invention concerns an orthodontic bite corrector for urging one of the dental arches either in a forward or rearward direction relative to the other dental arch.

2. Description of the Related Art

Orthodontic treatment involves movement of malpositioned teeth to orthodontically correct locations. Orthodontic treatment can improve the patient's occlusion so that the teeth of one jaw function in a satisfactory manner in cooperation with the teeth of the opposite jaw. In addition, teeth that are straightened by orthodontic treatment can significantly improve a patient's facial appearance.

One type of orthodontic treatment program includes a system of tiny appliances known as brackets. The brackets are connected to anterior, cuspid and bicuspid teeth, and an archwire is placed in a slot of each bracket. The archwire forms a track to guide movement of the brackets and the associated teeth to desired positions for correct occlusion. Typically, the ends of the archwire are received in appliances known as buccal tube brackets that are secured to molar teeth.

The orthodontic treatment of some patients includes correction of the alignment of the upper dental arch with the lower dental arch. For example, certain patients have a condition referred to as a Class II malocclusion where the lower dental arch is located an excessive distance in a rearward direction relative to the location of the upper dental arch when the jaws are closed. Other patients may have an opposite condition referred to as a Class III malocclusion wherein the lower dental arch is located in a forward direction of its desired location relative to the position of the upper dental arch when the jaws are closed.

Orthodontic treatment of Class II and Class III malocclusions are commonly corrected by movement of the upper dental arch as a single unit relative to the movement of the lower dental arch as a single unit. To this end, forces are often applied to each dental arch as a unit by applying force to the brackets, the buccal tubes or the archwires, or to attachment devices connected to the brackets, buccal tubes, or archwires. In this manner, a Class II or Class III malocclusion can be corrected at the same time that the archwires and the brackets are used to move individual teeth to desired positions relative to each other.

A number of devices are known in the art for correcting Class II and Class III malocclusions. Such bite correctors are sometimes referred to as Herbst appliances, bite jumpers, jaw repositioners and/or force modules. The bite correctors described in U.S. Pat. Nos. 4,551,095 (Mason) and 4,462,800 (Jones) and are constructed using telescoping tube assemblies that urge the dental arches toward positions of improved alignment. The telescoping tube assemblies are securely coupled to other orthodontic components in the oral cavity such as brackets, buccal tubes or archwires.

Another type of telescoping tube bite corrector for repositioning the dental arches is described in U.S. Pat. No. 5,964,588 (Cleary). The bite corrector described in this patent has a spring that urges telescoping members away from each other to achieve desired movement of the patient's teeth. Other patents that describe orthodontic telescoping tube assemblies with springs include U.S. Pat. Nos. 5,711,667 (Vogt), 5,562,445 (DeVincenzo et al.) and 3,798,773 (Northcutt).

While the above-known devices are deemed satisfactory by many practitioners, there is a continuing need in the art for improvements that facilitate the placement and operation of bite correctors. Preferably, any such improvements would also increase the versatility of the bite corrector so that it can be adapted for use in a variety of different situations with different patients. Moreover, it is preferable that any such improvements do not unduly increase the cost of the bite corrector or increase the likelihood that the patient will experience discomfort during the course of treatment.

SUMMARY OF THE INVENTION

The present invention relates to an orthodontic bite corrector that extends in close proximity to the patient's dental arch and has a relatively low profile. As a consequence, components of the bite corrector are less likely to impinge on adjacent soft tissue in the patient's oral cavity. The present invention increases patient comfort and reduces the risk of injury to soft tissue by remaining in an orientation that closely hugs the external surfaces of the patient's teeth.

More specifically, the orthodontic bite corrector of the present invention includes a telescoping assembly having a central, longitudinal axis that is curved. Preferably, the curvature of the telescoping assembly generally matches the curvature of the patient's jaws. The bite corrector remains in close proximity to the labial surfaces of the patient's teeth during opening and closing movement of the jaws and during the times that the jaws are at rest. Surprisingly, it has been found that a telescoping orthodontic bite corrector constructed according to the present invention does not bind or kink as the jaws are opened and closed even though the longitudinal axis of the corrector is curved.

In more detail, the present invention is directed toward an intraoral bite corrector for moving the relative positions of the upper and lower dental arches. The bite corrector comprises an inner member including a first body and a first coupling extending from the first body for connection to a first dental arch. The bite corrector also includes an outer member including a second body and a second coupling extending from the second body for connection to a second dental arch. The second body has a tubular configuration. The first body is received in the second body in telescoping relation, and the first body and the second body are rigid. The first body and the second body have central, longitudinal axes with matching, curved configurations.

These and other aspects of the invention are described in more detail below and are illustrated in the accompanying drawings.

DEFINITIONS

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Labial" means in a direction toward the patient's lips.
"Buccal" means in a direction toward the patient's cheeks.
"Lingual" means in a direction toward the patient's tongue.

DETAILED DESCRIPTION OF THE PREFERRED EMBODIMENTS

Figure 1:
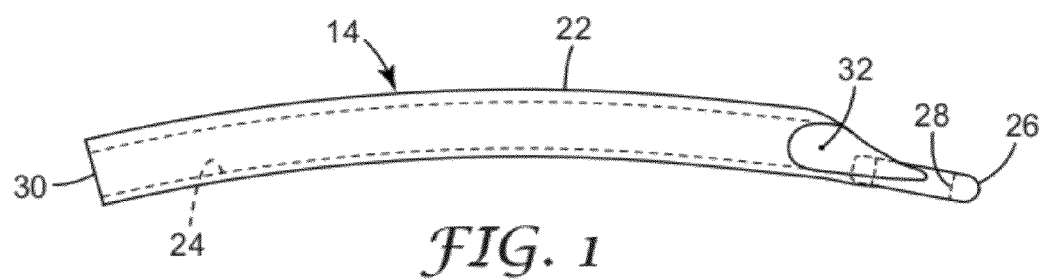
FIG. 1 is a bottom view of an outer member of an orthodontic bite corrector constructed in accordance with one embodiment of the present invention.
Figure 2:
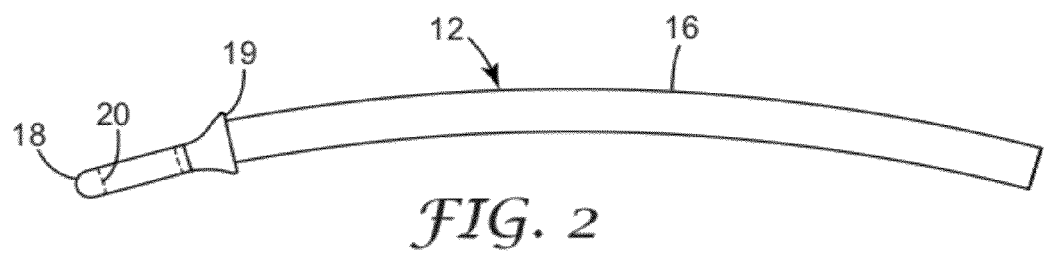
FIG. 2 is a bottom view of an inner member of the bite corrector for assembly with the outer member illustrated in FIG. 1.
Figure 3:
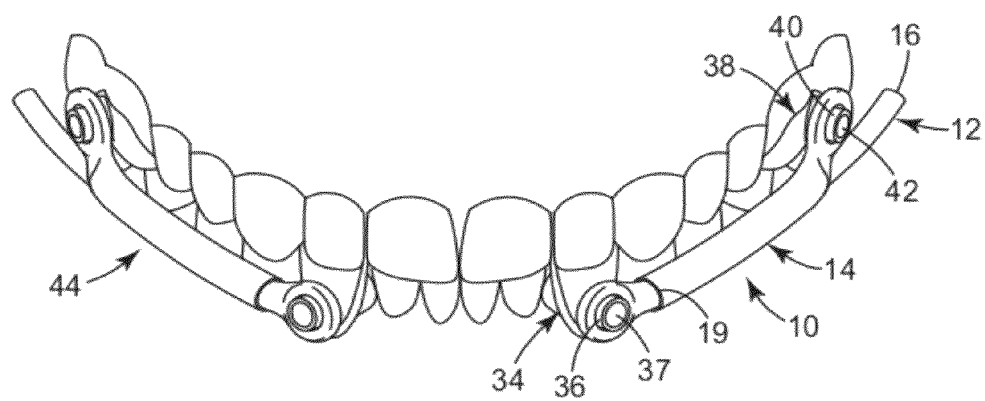
FIG. 3 is a reduced elevational view showing the bite corrector in place on the left side of the patient's dental arch, wherein the inner member and outer member shown in FIGS. 1 and 2 have been assembled together, and additionally showing a somewhat similar bite corrector in place on the right side of the patient's dental arch.
Figure 4:
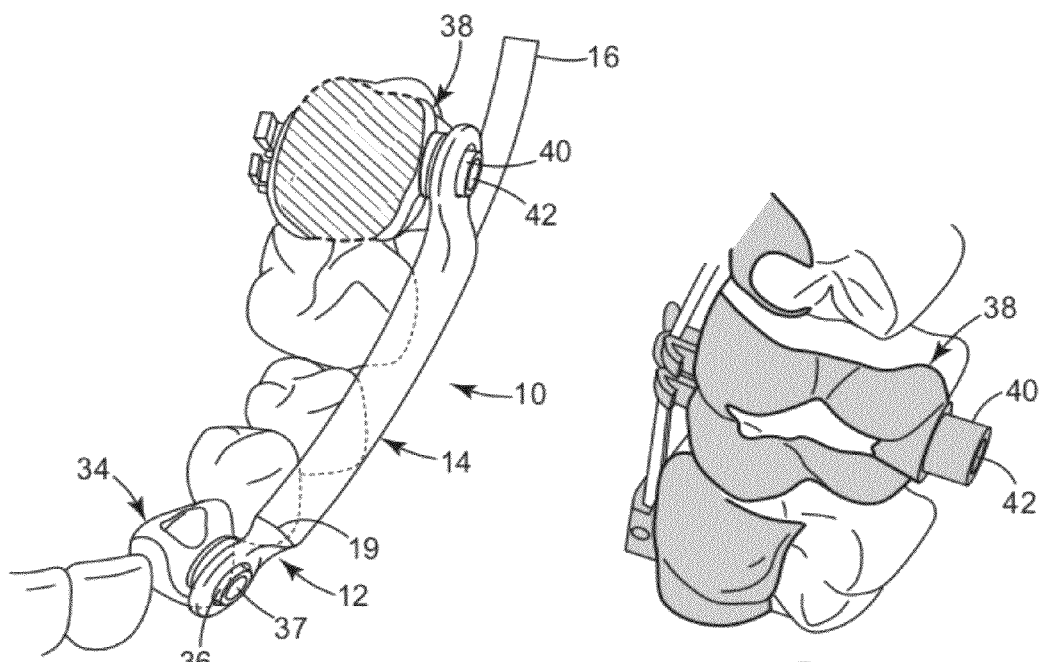
FIG. 4 is an enlarged top view in partial section of a portion of the left side of the patient's dental arch and the associated bite corrector of FIG. 3.

A low profile orthodontic bite corrector for moving the relative positions of the upper and lower dental arches is illustrated in FIGS. 3 and 4 and is designated by the numeral 10. The bite corrector 10 comprises an assembly that includes an inner member 12 (shown alone in FIG. 2) and an outer member 14 (shown alone in FIG. 1).

The inner member 12 includes a first elongated body 16 that has a circular cross-sectional configuration in the embodiment shown in FIG. 2. The inner member 12 also includes a first coupling 18 that extends outwardly from the first body 16 in general alignment with the longitudinal axis of the latter. The first coupling 18 includes a circular aperture 20 and resembles an eyelet. The inner member 12 also includes a conical-shaped collar 19 that is located between the first coupling 18 and the first body 16. The collar 19 has an outer diameter that is larger than the outer diameter of the first body 16.

The outer member 14 includes a second elongated body 22 that has a tubular configuration. The second body 22 includes an inner passageway 24 that extends along the central, longitudinal axis of the second body 22. The second body 22 optionally has a circular external configuration and a circular internal configuration when considered in reference planes perpendicular to the curved, central, longitudinal axis of the second body 22.

The outer member 14 includes a second coupling 26 that extends outwardly from the second body 22. The second coupling 26 is somewhat similar to the first coupling 18, in that the second coupling 26 includes an aperture 28 and resembles an eyelet. However, other types of couplings known to those in the art such as hooks, crimp-on connectors or the like may be used in place of the couplings 18, 26 that are illustrated in this embodiment.

The passageway 24 includes a mesial opening 30 at its mesial end and a distal opening 32 at its distal end. Preferably, and as shown for example in FIG. 3, the second coupling 26 extends at an angle relative to the central, longitudinal axis of the second body 22 such that the second coupling 26 is located in a position that is laterally offset from the body 22 and from the distal opening 32 in a gingival direction relative to the adjacent upper dental arch.

During assembly of the bite corrector 10, the distal end of the inner member 12 is inserted into the mesial opening 30 of the outer member 14. Continued movement of the inner member 12 in a distal direction relative to the outer member 14 serves to move the first body 16 along the passageway 24 until such time as the distal end of the inner member 12 emerges from the distal opening 32 of the outer member 14. In FIGS. 3 and 4, the inner member 12 is depicted in its fully retracted or collapsed position relative to the outer member 14, and in this orientation a distal end portion of the first body 16 extends in a distal direction from the distal opening 32 of the outer member 14. When the bite corrector is fully collapsed, the collar 19 of the inner member 12 is in abutting relation with the mesial end of the tubular second body 22.

Opposite end portions of the bite corrector 10 are connected to teeth of opposite jaws. In the exemplary embodiment shown in FIGS. 3-4, the first coupling 18 is coupled to a customized appliance 34 that is secured to the patient's lower left canine tooth. The appliance 34 extends over portions of the labial, occlusal and lingual surfaces of the canine tooth and is fixed to the tooth by means of an orthodontic adhesive. Optionally, and as depicted in FIG. 4, a central portion of the appliance 34 includes an opening for exposing a portion of the incisal edge of the canine tooth. As an additional option, the lingual side of the appliance 34 includes a bracket body (not shown) with an archwire slot for receiving a lingual archwire. Furthermore, the bracket body may optionally include one or more tiewings for ligating the archwire in place or may include one or more self-ligating latches for retaining the archwire in place.

The appliance 34 includes a cylindrical boss 36 that extends outwardly from the canine tooth in a labial direction. When the inner member 12 is connected to the appliance 34, the boss 36 extends through the aperture 20 and a screw such as a cap screw (not shown) is threaded into a threaded, axially-oriented hole 37 of the boss 36 in order to retain the inner member 12 in coupled relation to the appliance 34. The cap screw includes a round head having a diameter larger than the diameter of the boss 36, and the head extends over portions of the first coupling 18 surrounding the aperture 20 in order to provide a secure, pivotal connection between the first coupling 18 and the appliance 34. The screw head preferably includes a receptacle such as a slotted or hex-shaped receptacle for receiving a hand instrument in order to tighten and loosen the screw when desired.

Figure 5:
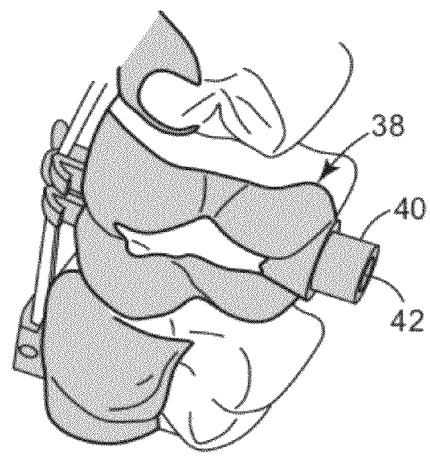
FIG. 5 is a fragmentary, perspective bottom view illustrating one type of appliance for connecting the bite corrector of FIGS. 1-4 to the patient's teeth.

A similar connection is made between the outer member 14 and a custom orthodontic appliance 38 that, in this embodiment, is fixed to the patient's upper first left molar tooth. As illustrated in FIG. 5, the appliance 38 includes a cylindrical boss 40 that extends outwardly in a buccal direction from the adjacent first molar tooth. The boss 40 includes a central, threaded hole 42 for receiving a screw such as a cap screw (not shown).

To connect the distal end of the outer member 14 to the appliance 38, the aperture 28 of the second coupling 26 is placed over the boss 40 and a cap screw is threaded into the hole 42. The cap screw covers a portion of the second coupling 26 adjacent the aperture 28 in order to releasably retain the outer member 14 in connected relation to the appliance 38. Since the outer surface of the boss 40 and the aperture 28 have circular shapes, a pivotal connection is established between the appliance 38 and the bite corrector 10.

As an option, the appliances 34, 38 as well as other orthodontic appliances used in the course of treatment are similar to appliances described in U.S. Patent Publication No. 2007/

0178423 (Rubbert et al.) and U.S. Pat. Nos. 6,776,614 (Wiechmann et al.), 6,928,733 (Rubbert et al.) and 7,240,528 (Weise et al.). As an alternative, the bite corrector 10 may be connected to other appliances that are fixed to other teeth in the patient's mouth, such as the first lower bicuspid tooth and the second upper molar tooth.

In practice, the length of the outer member 14 is selected such that the collar 19 contacts the mesial end of the outer member 14 before the patient's jaws are fully closed. Once such contact is established, further closing movement of the patient's jaws will urge the lower jaw in a forward direction relative to the upper jaw and thereby bring the jaws into alignment. Optionally, the outer member 14 is custom-made for each patient by determining the desired distance between the bosses 36, 40 when the patient's jaws are closed and in their orthodontically correct positions, and then constructing the outer member 14 such that the distance between the apertures 20, 28 matches the desired distance when the corrector 10 is fully collapsed. As yet another option, one or more bushings may be placed over the first body 16 before assembly of the bite corrector 10 in order to adjust and increase the distance as desired between the bosses 36, 40 when the patient's jaws are closed.

As can be appreciated by reference to FIGS. 3 and 4, the overall shape of the bite corrector 10 follows the natural curve of the patient's lateral dental arches. To this end, the curved, central longitudinal axis of the inner member 12 matches the curved, central longitudinal axis of the outer member 14, and the curvature of both longitudinal axes is similar to the curvature of adjacent regions of the patient's dental arches. As a consequence, the bite corrector 10 remains closely adjacent the labial surfaces of the upper and lower teeth regardless of whether or not the patient's jaws are opened or closed. The use of lingual brackets (such as brackets affixed to appliances 34, 38) in combination with the bite corrector 10 is a particular advantage, in that the bite corrector 10 does not come into contact with the brackets or archwires during the course of treatment.

Moreover, by providing a curved inner member 12, the first body 16 remains in close proximity to the patient's teeth when the jaws are closed and reduces the likelihood that the distal end of the first body 16 comes into contact with the patient's oral tissue even when the inner member 12 is fully retracted into the outer member 14. Such construction enables the length of the first body 16 to be increased to an extent such that the inner member 12 does not withdraw completely from the outer member 14 and disengage the latter when the patient's jaws are fully opened. As a result, the inner member 12 remains assembled to the outer member 14 during ordinary use and the progress of treatment is not interrupted.

In a typical treatment program, a second bite corrector 44 (see FIG. 3) is placed on the right side of the patient's jaws so that symmetrical forces are applied to the jaws during closing movements. Optionally, the second bite corrector 44 is similar to the bite corrector 10 in mirror image.

A number of other options are also possible. For example, one or more springs could be added to the bite corrector 10 in order to provide some initial force to the jaws before the members 12, 14 are fully collapsed and the collar 19 engages the mesial end of the outer member 14. Alternatively, or in addition, a sleeve may be provided between the inner member 12 and the outer member 14 so that the bite corrector includes three members that move relative to each other. For example, the present invention may be adapted for use with a three-member bite corrector such as the force module described in U.S. Pat. No. 5,964,588 (Cleary).

Surprisingly, the inner member 12 and the outer member 14 do not normally bind during opening and closing movements of the patient's jaws even though the central axes of the members 12, 14 are curved. As one example of construction, the first body 16 of the inner member 12 may have an outer diameter of 1.9 mm, the inner surface of the passageway 24 of the outer member 14 may have a diameter of 2.15 mm, and the radius of curvature of the bodies 16, 22 may be 70 mm. Such construction provides sufficient free play to enable opening and closing movements of the bite corrector without undue resistance.

Optionally, the bite corrector 10 may be provided with key and keyway structure to retain the axial orientation of the inner member 12 in fixed relation to the axial orientation of the outer member 14. For example, the passageway 24 may include a longitudinal groove, and the body 16 may include an elongated protrusion that is slidably received in the groove. The key and keyway structure may be preferred when the couplings 18, 26 are replaced with couplings of another type.

As an additional option, one or both of the members 12, 14 may be provided with a coating that reduces sliding friction between the members 12, 14. Alternatively, the bite corrector 10 may include bushings, sleeves or sliding members made of a polymeric material such as polytetrafluoroethylene to reduce sliding friction between the members 12, 14. Other materials are also possible. However, it is believed that saliva that is present in the oral cavity is sufficient to provide any lubrication that is normally needed.

All of the patents and patent applications identified above are hereby incorporated by reference into the present disclosure. Those skilled in the art may recognize that other variations and additions may be made to the bite corrector 10 described above without departing from the essence of the invention. As such, the invention should not be deemed limited to the specific, preferred embodiments set out above, but instead only by a fair scope of the claims that follow along with their equivalents.

The invention claimed is:

1. An orthodontic bite corrector for moving the relative positions of the upper and lower dental arches comprising:
    an inner member including a first rigid body having a mesial end and a distal end, a first coupling extending from the first body for connection to a first dental arch, and a collar proximate the mesial end of the first body, the collar including an outer diameter that is larger than a outer diameter of the first body; and
    an outer member including a second rigid body and a second coupling extending from the second body for connection to a second dental arch, wherein the second body has a tubular configuration and wherein the first body is received in the second body in telescoping relation, wherein the first body and the second body have central, longitudinal axes with matching, curved configurations, wherein the outer member has a central, elongated passageway with an opening adjacent each end of the passageway for passage of the inner member, and wherein the first body includes a length greater than the length of the outer member and the distal end extends past the second coupling.

2. An orthodontic bite corrector according to claim 1 wherein the curved configurations generally match the curvature of a patient's dental arches.

3. An orthodontic bite corrector according to claim 1, wherein the passageway of the second body comprises a diameter no greater than 0.25 mm larger than an outer diameter of the first body.

4. An orthodontic bite corrector according to claim 1 wherein the first coupling is integrally connected to the first body and wherein the second coupling is integrally connected to the second body.

5. An orthodontic bite corrector according to claim 1 wherein the orientation of the first coupling to the first body is fixed and wherein the orientation of the second coupling to the second body is fixed.

6. An orthodontic bite corrector according to claim 1 wherein at least one of the couplings comprises an aperture.

7. An orthodontic bite corrector according to claim 1, wherein the collar is conical-shaped.

8. An orthodontic bite corrector according to claim 7 wherein the first body extends through both openings when the first body is fully received in the second body.

9. An orthodontic bite corrector according to claim 8 wherein the second coupling includes an occlusal side, and wherein the first body extends along the occlusal side of the second coupling when the first body is fully received in the second body.

10. An orthodontic system including a plurality of lingual brackets and at least one of the orthodontic bite correctors of claim 1.

11. An orthodontic system according to claim 10 and including an upper appliance for connection to one of the teeth of the upper dental arch and a lower appliance for connection to one of the teeth of the lower dental arch, wherein one of the couplings is connected to the upper appliance and wherein the other of the couplings is connected to the lower appliance, and wherein at least one of the lingual brackets is connected to the lower appliance.

12. An orthodontic system according to claim 11 wherein at least one of the lingual brackets is connected to the upper appliance.

13. An orthodontic system according to claim 11 wherein at least one of the appliances includes a lingual surface that is custom-made and has a contour that matches a lingual surface of a patient's tooth.

14. An orthodontic bite corrector according to claim 1, wherein the radius of curvature of the first and second bodies is 70 mm.

15. An orthodontic bite corrector according to claim 1, wherein the first body and the second body do not normally bind during opening and closing movements of the patient's jaws.

16. An orthodontic bite corrector according to claim 1, wherein the bite corrector remains closely adjacent the labial surfaces of the upper and lower teeth when the jaws are opened or closed when the corrector is secured to a patient's dental arches.

* * * * *